United States Patent [19]

Greven et al.

[11] 4,110,322

[45] Aug. 29, 1978

[54] PEPTIDE DERIVATIVES AND PHARMACEUTICAL COMPOSITIONS CONTAINING SAME

[75] Inventors: Hendrik Marie Greven, Heesch; David de Wied, Bilthoven, both of Netherlands

[73] Assignee: Akzona Incorporated, Asheville, N.C.

[21] Appl. No.: 810,277

[22] Filed: Jun. 27, 1977

[30] Foreign Application Priority Data

Jul. 12, 1976 [NL] Netherlands ............... 7607683

[51] Int. Cl.$^2$ ............... C07C 103/51; A61K 37/00; C07G 7/00
[52] U.S. Cl. ............... 260/112.5 R; 424/177
[58] Field of Search ............... 260/112.5 R; 424/177

[56] References Cited

U.S. PATENT DOCUMENTS 3,853,838 12/1974 Greven ............... 260/112.5 R

*Primary Examiner*—Delbert R. Phillips
*Assistant Examiner*—Blondel Hazel
*Attorney, Agent, or Firm*—Robert H. Falk; Charles A. Wendel; Francis W. Young

[57] ABSTRACT

Biologically active novel peptide compounds are disclosed of the formula

A-L-B-D-Lys-L-Phe-Gly-(L or D)Lys-L-Pro-L-Val-Gly-L-Lys-L-Lys-X or a pharmaceutically acceptable non-toxic functional derivative thereof; A is a N-terminal chain prolongation selected from the group consisting of (1) hydrogen and (2) N-acyl radicals derived from (a) alkyl carboxylic acids having from one to about six carbons, (b) aralkyl carboxylic acids having from seven to about ten carbons, (c) amino acids, (d) peptides, (e) the N-alkylcarbonyl or N-aralkylcarbonyl derivatives of the amino acids, and (f) the N-alkylcarbonyl or N-aralkylcarbonyl derivatives of the peptides; B is an amino-acid residue selected from the group consisting of Phe, Trp, Tyr, and —NH—CHR$_1$—CO—, wherein R$_1$ is hydrogen or alkyl from one to about six carbons; and X is a member selected from the group consisting of hydroxy, esterified hydroxy radicals, unsubstituted amino radicals and substituted amino radicals. Pharmaceutical compositions containing these compounds are also disclosed to take advantage of the valuable psychopharmacological properties thereof, such as utilization for the treatment for senility or, more generally, for a stimulation of the mental performance.

34 Claims, No Drawings

PEPTIDE DERIVATIVES AND PHARMACEUTICAL COMPOSITIONS CONTAINING SAME

BACKGROUND TO THE INVENTION

1. Field of the Invention

This invention relates to the field of pharmaceutical compounds, and to the sub-field of psychopharmacologically active compounds. The compounds in question show an inhibition of the extinction of conditioned flight behaviour, as a result of which they are eminently suitable for the treatment of mental disorders in which a stimulation of the cerebral function is desired, such as in case of senility. The invention further relates to pharmaceutical compositions containing these peptide compounds or their derivatives where the latter are an active constituent.

2. Description of the Prior Art

From EUROPEAN JOURNAL OF PHARMACOLOGY 2, 14 (1967) it is known that the natural adrenocorticotropic hormone (ACTH), and more specifically certain peptide fragments thereof, retard the extinction of the so-called "conditioned flight behaviour". In particular, the peptide containing the amino-acid sequence 4–10 from ACTH proved to be the smallest peptide fragment which was as active as ACTH itself in this respect.

From the U.S. Pat. No. 3,853,836 it appears, however, that the complete amino-acid sequence 4–10 ACTH is not essential for psychopharmacological activity but that a much shorter peptide, namely, 4–6 ACTH, is responsible for this activity. It furthermore appears that the N-terminal amino-acid L-Met may be replaced without loss of activity by D-Met, L- or D-Met (→ O), L- or D-Met (→ $O_2$), desamino-Met, desamino-Met (→ O), desamino-Met (→ $O_2$) or by the group

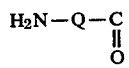

where Q represents an alkylidene moiety having from one to about six carbon atoms or an alkylene moiety having from one to about six carbons.

It is furthermore taught in U.S. Pat. No. 3,856,770 that the replacement of the C-terminal peptide residue -L-Trp-Gly-OH of the original 4–10 ACTH peptide by one of the groups consisting of -L-Phe-OH, L-Phe-Gly-OH, a phenylalkylamino moiety or a (3-indolyl) alkylamino moiety results in an increase in psychopharmacological activity.

It is further reported in the U.S. Pat. No. 3,842,064 that a considerable increase in psychopharmacological activity is obtained on replacing the amino-acid L-arginine (L-Arg) in the original 4–10 ACTH peptide (or in one of the modified peptides described in the above-noted patent specifications) by D-lysine (D-Lys).

One of the most active peptides named in the above-noted U.S. Patents is the peptide represented by the abbreviation:

4–9 ACTH, 4-L-Met (→ O), 8-D-Lys, 9-L-Phe, a peptide which with respect to the original 4–9 ACTH has been changed in accordance with the potentiation noted in the patent specifications in positions 4, 8 and 9.

This peptide, to wit

H-L-Met (→ O)-L-Glu-L-His-L-Phe-D-Lys-L-Phe-OH, proves to be about 1000 times as active as the unchanged 4–9 ACTH.

It has now been found that the peptide-fragment of this 4–9 ACTH, 4-L-Met(→ O), 8-D-Lys, 9-L-Phe, to wit the fragment:

L-Phe-D-Lys-L-Phe in itself also occasions some psychopharmacological activity, although in a latent form. On the basis of U.S. Pat. No. 3,856,770 and U.S. Pat. No. 3,842,064 it is recognized by those skilled in the art that a highly active peptide is(was) obtained by lengthening the chain of the peptide L-Phe-D-Lys-L-Phe at the N-terminal end, for example, with the peptide fragment L-Met(→ O)-L-Glu-L-His:

L-Met(→ O)-L-Glu-L-His-L-Phe-D-Lys-L-Phe

Surprisingly, it has now also been found that highly active peptides can be obtained by lengthening the chain at the C-terminal end of the peptide L-Phe-D-Lys-L-Phe. This pronounced potentiation (with a factor of at least 1000) on lengthening the chain at the C-terminal end was not to be expected to those skilled in the art on the basis of the information known until now. (It has after all been shown that C-terminal chain prolongation of the original 4–10 or 4–9 ACTH resulted in no potentiation of effect whatsoever - see e.g. European Journal of Pharmacology 2, 14 (1967) - while it turned out that C-terminal chain prolongation of the 7–9 ACTH peptide increased the activity at most by a factor 10. This surprising activity can be illustrated by means of the example given in the table below:

TABLE I

| | Peptide | Potency Ratio with Respect to 4–10 ACTH |
|---|---|---|
| 1. | Met-Glu-His- Phe-Arg-Trp (4–9 ACTH) | 1 |
| 2. | Phe-Arg-Trp (7–9 ACTH) | 0.1 |
| 3. | Phe-Arg-Trp-Gly-Lys-Pro-Val-Gly-Lys-Lys (7–16 ACTH) | 1 |
| 4. | Phe-D-Lys-Phe | 0.1 |
| 5. | Phe-D-Lys-Phe-Gly-Lys-Pro-Val-Gly-Lys-Lys | 100 |

Furthermore, we demonstrated that the lengthening of the chain at the C-terminal end of the above peptide L-Phe-D-Lys-L-Phe proved to be of high significance in the sense that a minimum C-terminal chain length is essential. This minimum lengthening of the chain proved surprisingly to be the peptide 10–16 ACTH; a shorter chain length reduced the activity to a level corresponding to that seen with unaltered 7–16 ACTH.

We furthermore surprisingly found that a still more considerable potentiation could be achieved by replacing the amino-acid L-Lys (position 11) in the minimum essential C-terminal chain lengthening (10–16 ACTH) by the amino-acid D-Lys. This modification increases the activity of the peptide by a further factor of 100. These facts are clearly illustrated by the following example in table II:

TABLE II

| | Peptide | Potency Ratio with Respect to 4–10 ACTH |
|---|---|---|
| 1. | Phe-Arg-Trp-Gly-Lys-Pro-Val-Gly-Lys-Lys (7–16 ACTH) | 1 |
| 2. | Phe-D-Lys-Phe-Gly-Lys-Pro-Val-Gly-Lys-Lys | 100 |
| 3. | Phe-D-Lys-Phe-Gly-Lys-Pro-Val-Gly-Lys | 1 |
| 4. | Phe-D-Lys-Phe-Gly-D-Lys-Pro-Val-Gly-Lys-Lys | 10,000 |

The peptide L-Phe-D-Lys-L-Phe, the activity of which may be substantially increased as stated above by lengthening the C-terminal chain, may be further potentiated by additional N-terminal chain lengthening in methods described in U.S. Pat. No. 3,853,836, U.S. Pat. No. 3,856,770, and U.S. Pat. No. 3,842,064, which methods and specific additional lengths are incorporated herein by reference as if copied verbatim. The resultant peptides prove to possess psychopharmacological activity which is $10^6$ to $10^7$ times as strong as that of the original 4–10 ACTH peptide.

It has furthermore been found that the first amino-acid Phe in the original L-Phe-D-Lys-L-Phe does not necessarily have to be present, but it may also be replaced by numerous other amino-acids, so that the primary advantages of this amino-acid evidently come from the provision of the additional right chain length.

SUMMARY OF THE INVENTION

The preparation and application of novel biologically active and stable compounds (and functional derivatives thereof) of the formula A-L-B-D-Lys-L-Phe-Gly-(L or D)-Lys-L-Pro-L-VaL-Gly-L-Lys-L-Lys-X (I) wherein A is a N-terminal chain prolongation selected from the group consisting of (1) hydrogen and (2) N-acyl radicals derived from (a) alkyl carboxylic acids having from one to about six carbons, (b) aralkyl carboxylic acids having from seven to about ten carbons, (c) amino acids, (d) peptides, (e) the N-alkylcarbonyl or N-aralkylcarbonyl derivatives of the amino-acids, and (f) the N-alkylcarbonyl or N-aralkylcarbonyl derivatives of the peptides; B is an amino-acid residue selected from the group consisting of Phe, Trp, Tyr, and —NH—CHR$_1$—CO—, wherein R$_1$ is hydrogen or alkyl from one to about six carbons; and X is a member selected from the group consisting of hydroxy, esterified hydroxy radicals, unsubstituted amino radicals and substituted amino radicals.

It is an object of this invention to prepare these compounds for the utilization of their psychopharmacological properties in the treatment in humans for mental disorders, in which stimulation of the cerebral function is desired, such as for senility.

It is a further object of this invention to prepare pharmaceutical compositions having one or more compounds of formula (I) in a pharmaceutically accepted carrier for the treatment of mental disorders, in which a stimulation of the cerebral function is desired, such as for senility.

DESCRIPTION OF THE PREFERRED EMBODIMENTS

Examples for R$_1$ in formula I above may include hydrogen, methyl, isopropyl, isobutyl and sec.-butyl for example.

In the definition of B the preferred amino-acid residues are Phe and Ala, the latter being derived from —NH—CHR$_1$—CO—, in which R$_1$ is methyl.

In the definition of X in the same formule I, examples for an esterified hydroxy group may include the esters derived from aliphatic alcohols such as methanol, ethanol, propanol, butanol, hexanol, decylalcohol, laurylalcohol, myristylalcohol and stearylalcohol. In general, the esterified hydroxy group will have from one to about eighteen carbon atoms, and preferably from one to about eight carbon atoms.

The substituted amino group referred to in the definition of X includes a mono- or dialkyl-amino group, in which the alkyl group contains from one to about six carbon atoms, such as methylamino, dimethylamino, diethylamino, isopropylamino, butylamino, isobutylamino, sec.-butylamino, n-pentylamino and n.hexylamino, but also includes an amino-acid or peptide residue with the sequence 17, 17-18, 17-19 etc. up to and including 17-24 ACTH or the corresponding C-terminal ester or amide thereof, with the proviso that the amino-acid residue Arg (present at the positions 17 and 18 of the ACTH fragment) may optionally be replaced by Lys.

In the definition of A, the N-acyl group may be derived from any alkyl carboxylic acid from one to about six carbon atoms such as acetic acid, propionic acid, valeric acid, and caproic acid, for example. In the alternative, A may be any acyl group derived from an aralkyl carboxylic and having from seven to about ten carbons, such as phenylacetic acid, phenylpropionic acid, and phenylbutyric acid, for example. As a further alternative, the N-acyl group may also be derived from an amino acid or peptide.

Finally, A may be a N-alkylcarbonyl (alkyl is from one to about six carbons) or N.aralkylcarbonyl (aralkyl is from seven to about ten carbons) derivative of said amino acid or said peptide residue. In formula (I) above, the term D-Lys-L-Phe-Gly-(L or D)-Lys-L-Pro-L-Val-Gly-L-Lys-L-Lys may be referred to hereinafter and in the Claims as the "basic unit omitting extension." In this basic unit omitting extension, one will notice that there are four lysine units, and that speaking first from the N-terminal end toward the C-terminal end, the first lysine group must be in its D form, the third and fourth groups must be in their L form, while the second group according to our invention may be in a L or D form. The nomenclature A and B may be referred to hereinafter as "N-terminal chain prolongation," while X may be referred to as the "C-terminal end prolongation."

N-Acyl derivatives (in the definition of A) which are preferred are derived from an amino acid or peptide and consist of one to three amino-acid residues consisting of the group U-Q$_1$-, U-Q$_2$-Q$_1$, and Q$_3$-Q$_2$-Q$_1$-, wherein U is selected from the group consisting of hydrogen, and N-alkylcarbonyl of from one to about six carbons or N-aralkylcarbonyl of from seven to about ten carbons; $Q_1$ is selected from the amino-acid residue consisting of L-His, D-His, or —NH—Z—CO; $Q_2$ is selected from the amino-acid residues consisting of L-Glu, D-Glu, L-Gln, D-Gln or —NH—Z—CO—; and $Q_3$ is the acid residue U-L-Met, U-L-Met(→ O), U-L-Met(→ $O_2$), U-D-Met, U-D-Met(→ O), U-D-Met(→ $O_2$), desamino-Met, desamino-Met(→ O), desamino-Met(→ $O_2$) or UNH—Z—CO—, Z represents an unsubstituted, monohydroxy substituted, or mono-amino substituted alkylene or alkylidene moiety with one to about six carbon atoms.

Amino-acid residues, such as Gly, Ala, $\beta$-Ala, ($\alpha$-Me)Ala, Val, Leu, Ile, Ser, Thr and Lys are deemed to belong to the amino-acid residue defined by the formula —NH—Z—CO—.

N-Acyl groups which are most preferred conform to the schematic representation $Q_3$-$Q_2$-$Q_1$-, wherein $Q_3$ is in this case derived from methionin or desaminomethionine (for example, L-Met, L-Met(→ O), L-Met(→ $O_2$), desamino-Met, desamino-Met(→ O) and desamino-Met(→ $O_2$), and where the sequence —$Q_2$—$Q_1$ represents the peptide residue —Glu—His—, or in the alternative, a peptide residue built up from 2 aliphatic and preferably identical natural amino acids, such as —Gly—Gly—, —Val—Val—, —Glu—Ala— and in particular —Ala—Ala—.

A group of peptides according to the teneral formula I which is therefore preferred can be represented by the following formula: $Q_3$-$Q_2$-$Q_1$-L-B-D-Lys-L-Phe-Gly-(L or D)-Lys-L-Pro-L-Val-Gly-L-Lys-L-Lys-X (II) or a functional derivative thereof, in which $Q_1$, $Q_2$, $Q_3$, B and X have the meanings assigned above.

By functional derivatives are understood: (a) salts or acid addition salts of the peptides according to general formula I or II, preferably the alkali metal salts and the pharmacologically active acid addition salts and (b) metal complexes, formed by bringing the peptides herein referred to into contact with an insoluble or slightly soluble salt, hydroxide or oxide of a metal (preferably zinc). By "alkali metal salts", we of course mean the salts of the metals from Group I of the Periodic Table. Pharmacologically acceptable acid addition salts include, for example, the HCl salt, HBr salt, phosphoric acid salt, acetic acid salt, tartaric acid salt, citric acid salt, etc.

As previously stated for formula I compounds, the esterified hydroxy group in the definition of X for formula II compounds generally represents an ester derived from aliphatic alcohols with one to about eighteen carbon atoms, and in particular those esters derived from aliphatic alcohols with one to about eight carbon atoms, such as methanol, ethanol, propanol, butanol, etc. The substituted amino group referred to in the definition of X is generally a mono- or di-alkyl substituted amino group, in which the alkyl groups contain one to about sic carbon atoms, but it may also be an amino-acid or peptide residue with the sequence 17, 17-18, 17-19, etc., up to and including 17-24 ACTH or the corresponding C-terminal ester or amide thereof, in which Arg may optionally be replaced by Lys. In the definition of B in formula II the preferred amino acid residues are Phe or Ala.

The peptides and peptide derivatives according to the general formula I (and also for formula II) are prepared in the way usual for such compounds. The most usual ways for the preparation of the compounds of formulas I and II referred to herein may be summarized in two types as follows: (a) Condensation in the presence of a condensation agent of a compound (acid, peptide, for example) possessing a free carboxyl group, and in which other reactive groups have been protected, with a compound (amino-acid, peptide or amine, for example) possessing a free amino group, and in which other reactive groups have likewise been protected, or (b) Condensation of a compound (acid, peptide, for example) possessing an activated carboxyl group, and in which other reactive groups have optionally been protected, with a compound (amino-acid, peptide, amine, for example) possessing a free amino group, and in which other reactive groups have similarly optionally been protected, after which the protective groups may be removed, if desired.

The most usual methods for the above-noted two types of condensation reactions are: the carbodi-imide method, the azide method, the mixed anhydride method and the activated esters method, as described in "The Peptides", Volume I, 1965 (Academic Press), E. Schröder and K-Lübke, incorporated herein as if written verbatim. The so-called "solid phase" method of Merrifield, described in J. Am. Chem. Soc. 85, 2149 (1963) and incorporated herein may furthermore be used for the preparation of the peptides or peptide derivatives of formulas I and II herein referred to. As these references will indicate, ways of activating the carboxyl group include conversion of the carboxyl group into an acid halide, an azide, anhydride, imidazolide or an activated ester (such as the N-hydroxysuccinimide ester or p-nitrophenyl ester). Similarly, these references show that the amino group may be activated by the conversion of same into a phosphinamide or by use of the "phosphorazo" method. As shown in the references cited and as appreciated by those skilled in the art, the reactive groups which must be prevented from participating in the condensation reaction, are effectively protected by the so-called protective groups, which may in their turn be readily removed by hydrolysis or reduction. A carboxyl group may, for example, be effectively protected by esterification with, for example, methanol, ethanol, tertiary butanol, benzyl alcohol or p-nitrobenzyl alcohol, or by conversion into an amide. This latter is, however, very difficult to remove, so that it is recommendable to use this group only for the protection of the carboxyl group of the C-terminal amino-acid in the final peptide or the $\gamma$-carboxyl group of glutamic acid. In this case, the peptide synthesis leads directly to the amide of the peptide according to formulas I or II.

Groups which can effectively protect an amino group are generally acid groups, for example an acid group derived from (a) an aliphatic, aromatic, araliphatic or heterocyclic carboxylic acid, such as an acetyl, benzoyl or pyridinecarboxyl group, (b) an acid group derived from carbonic acid, such as an ethoxycarbonyl, benzyloxycarbonyl, t-butyloxycarbonyl or p-methoxy benzyloxycarbonyl group, or (c) an acid group derived from a sulphonic acid, such as benzene-sulphonyl or p-toluene-sulphonyl; other groups may also be used, such as substituted or unsubstituted aryl or aralkyl groups, for example, benzyl and triphenylmethyl, or groups such as o-nitrophenylsulphenyl and 2-benzoyl-1-methylvinyl.

It is strongly recommended to protect also the $\epsilon$-amino group of lysine, the $\gamma$-carboxyl group of Glu and, if desired, the imidazole group of histidine. Usual protecting groups in this connection are a tertiary-butyloxycarbonyl or a tosyl group for the ε-amino group of lysine, a tert. butyloxycarbonyl group for Glu and a benzyl or trityl group for His.

The protective groups may be split off by various conventional methods known to those skilled in the art, depending on the nature of the group concerned, for example, with the aid of trifluoro-acetic acid, or by mild reduction, for example, with hydrogen and a catalyst, such as palladium, or with HBr in glacial acetic acid.

Ways of preparing peptides according to the present invention in which the N-terminal residue is (L or D)Met(→ O) or desamino-Met(→ O) can include mild oxidation, in a known way, or the corresponding Met or desamino-Met peptide, for example, with dilute hydrogen peroxide or a peracid. Such an oxidation gives a mixture of the S- and R-sulphoxide, which may be resolved into the separate diastereo-isomers by a known method, for example, by selective crystallization. By coupling (L or D)-methionine-S-(or -R-)-sulphoxide or the corresponding desamino derivative thereof with the remainder of the peptide fragment, the separate diastereo-isomers may also be obtained directly.

The peptides according to the present invention having (L or D)-Met(→ $O_2$) or desamino-Met(→ $O_2$) as the N-terminal residue, may be obtained by oxidation of the (desamino)Met-peptide I or by coupling of Met- or desamino-Met-sulphone with the remainder of the peptide fragment.

The acid addition salts are obtained by reaction of the peptides herein referred to with a pharmaceutically acceptable acid such as a hydrogen halide, phosphoric acid, acetic acid, tartaric acid or citric acid.

The peptides according to the invention and the derivatives defined above may be administered both orally and parenterally. For the purpose of parenteral administration, the peptides are dissolved, suspended or emulsified in a suitable fluid. When mixed with suitable excipients or fillers, they may be processed to give a form suitable for oral administration, such as pills, tablets or dragrees. The peptides herein referred to may also be administered in the form of a suppository or spray. The oral administration form is preferred. Examples of suitable fluids for parenteral administration include sterilised water, made isotonic and optionally buffered at about pH = 4, or oils, such as arachis oil. Examples of suitable excipients and fillers are lactose, mannitol, starch, magnesiumstearate, etc.

The peptides or peptide derivatives according to the invention are preferably used parenterally in a dosage of about 0.1 pg to 1 μg per kg body weight per day, and orally from about 1 μg to 1 mg per kg body weight per day, dependent on the peptide's activity level.

Particularly valuable preparations are obtained if the peptides herein referred to are incorporated into a form in which they give prolonged activity, i.e., in the so-called "time-capsules". The metal complexes of the peptides are specifically suitable to bring about this prolonged activity. These metal complexes may be obtained by bringing the peptides into contact with poorly soluble metal salts, metal hydroxides or metal oxides. The metals which may be used in this process are those metals which belong to Period 4 of the Periodic Table in the "b-groups" (transition element) for example, cobalt, nickel, copper, iron and (preferably) zinc, just as metals which belong to the "a-groups" of Period 3 of the Periodic Table and which are capable of forming complexes, such as magnesium and aluminium.

The preparation of these metal complexes takes place in ways known to those skilled in the art.

The metal phosphates, metal pyrophosphates and metal polyphosphates are preferably employed as poorly soluble metal salts. A metal complex may, for example, be obtained by adding the peptide and a molar excess of a poorly soluble metal salt, metal hydroxide or metal oxide to an aqueous medium. The metal complex may also be obtained by adding an alkaline medium to an aqueous solution of the peptide and a molar excess of the soluble metal salt, resulting in the formation of the insoluble peptide-metal hydroxide complex. The metal complex may furthermore be obtained by adding the peptide, an excess of a soluble metal salt and a soluble salt (not a "metal" salt as defined above) to an aqueous, preferably alkaline, medium, as a result of which an insoluble peptide-metal salt complex is formed in situ. The metal complexes may be used directly as suspensions or they may, for example, be freeze-dried and later resuspended again.

The following remarks are made with respect to all of the Specification, and in particular to the Examples, the Claims appended hereto and with regard to Tables I and II above:

1. If no optical configuration is given, the L-form is intended.

2. The following abbreviations have been assigned to the protective or activating groups used:
Boc = tertiary-butyloxycarbonyl
tBu = tertiary butyl
Me = methyl
ONP = p-nitrophenyloxy
Bzl = benzyl
ONB = nitrobenzyloxy
OSu = succinimido-N-oxy
Z = benzyloxycarbonyl 3. The following abbreviations have been assigned to the solvents or reagents used:
Bz = benzene
To = toluene
EtOH = ethanol
Bu = butanol
Py = pyridine
Ac = acetic acid
EtOAc = ethyl acetate
Wa = water
Am = amyl alcohol
iPro = isopropanol
DMF = dimethylformamide
THF = tetrahydrofuran
DCCI = dicyclohexylcarbodi-imide
DCHU = dicyclohexylurea
TAA = tri-ethylamine
TFA = trifluoroacetic acid
HOOBt = 3-hydroxy-4-oxo-3,4-dihydro-1,2,3-benztriazine
NEM = N-ethylmorpholine
HOBt = N-hydroxybenztriazole 4. The following abbreviations have been used for the amino-acid groups:
Met = methionyl
Met(→ O) = sulphoxide of methionyl
Met(→ $O_2$) = sulphone of methionyl
Glu, or Gln = glutamyl (glutamic acid) or glutaminyl respectively
Ser = seryl
His = histidyl
Phe = phenylalanyl Arg = arginyl
Lys = lysyl
Trp = tryptophyl
Gly = glycyl
Val = valyl
Leu = leucyl
Ala = alanyl
Ile or Ileu = isoleucyl
β-Ala = β-alanyl
(α-Me)Ala = α-methylalanyl
Pro = prolyl
Tyr = tyrosyl
Thr = threonyl 5. The following abbreviations have been used for groups related to amino-acid residues:
desamino-Met = desamino-methionyl
desamino-Met(→ O) = sulphoxide of desamido-methionyl (or 4-methylsulphinylbutyryl)
desamino-Met(→ $O_2$) = sulphone of desamino-methionyl, (or 4-methylsulphonylbutyryl).

Preparation of starting materials

I. N-terminal part

A. Peptides with the structural formulae given below are known from the U.S. Pat. Nos. 3.853.836, 3.856.770 and 3.842.064, the teachings of which are incorporated herein by reference.

1. Boc-Met-Glu(OtBu)-His-$N_2H_3$: Rf in Am:iPro:Wa (10:4:5) = 0.39 ($SiO_2$)
2. Boc-Met (→$O_2$)-Glu(OtBu)-His-$N_2H_3$; Rf in Am:i-Pro:Wa (10:4:5) = 0.36
3. Boc-Val-D-Glu(OtBu)-His-$N_2H_3$; Rf in Am:i-Pro:Wa (10:4:5) = 0.33
4. Boc-Gly-Glu(OtBu)-His-$N_2H_3$; Rf in Am:iPro:Wa (10:4:5) = 0.32
5. Boc-D-Met-Glu(OtBu)-His-$N_2H_3$; Rf in Am:iPro:Wa (10:4:5) = 0.37
6. Boc-β-Ala-Glu(OtBu)-His-$N_2H_3$; Rf in Am:i-Pro:Wa (10:4:5) = 0.42
7. Boc-(α-Me)Ala-Glu(OtBu)-His-$N_2H_3$; Rf in Am:i-Pro:Wa (10:4:5) = 0.31
8. Boc-Ala-Glu(OtBu)-His-$N_2H_3$; Rf in Am:iPro:Wa (10:4:5) = 0.33
9. Boc-Met-Glu(OtBu)-D-His-$N_2H_3$; Rf in Am:i-Pro:Wa (10:5:4) = 0.35
10. Boc-Val-Glu(OtBu)-D-His-$N_2H_3$; Rf in Am:i-Pro:Wa (10:4:5) = 0.32
11. Boc-Met-Gln-His-$N_2H_3$; Rf in Am:iPro:Wa (10:4:5) = 0.28
12. Desamino-Met-Glu(OtBu)-His-$N_2H_3$; Rf in Bu:Ac:Wa (4:1:1) = 0.52
13. Desamino-Met-Glu(OtBu)-D-His-$N_2H_3$; Rf in Bu:Ac:Wa (4:1:1) = 0.50
14. Boc-Met-Ala-Ala-$N_2H_3$ (a) Boc-Ala-Ala-OMe: 20.79 g Boc-Ala-OH is dissolved in 150 ml DMF. After cooling to −10° C, 15.84 ml TAA is added, followed by 10.45 ml ethyl chloroformate. The mixture is stirred at −10° C for 10 minutes, after which a solution of 13.9 g H-Ala-OMe-HCl in 150 ml DMF and 14.4 ml TAA is added dropwise. The reaction mixture is now stirred by suitable mechanical means for 15 minutes at −10° C, 2 hours at 0° C and finally for 8 hours at room temperature. After cooling to −10° C, the TAA-HCl is filtered off and the filtrate is evaporated to dryness. The residue is dissolved in 250 ml ethyl acetate and washed consecutively with water, HCl (0.05N), $K_2CO_3$ solution (5%) and NaCl solution (30%). After drying over $Na_2SO_4$, the filtrate is evaporated to dryness and the residue is crystallized from ether/ p.ether. Yield 19.3 g; melting point 108/110° C. Rf in To:EtOH (8:2) = 0.50 on $SiO_2$.

(b) H-Ala-Ala-OMe.HCl: 18.75 g Boc-Ala-Ala-OMe (from (a)) is dissolved in 150 ml methylene chloride and HCl is passed into the solution for 45 minutes, during which time it is kept cool in ice-water. Yield of the deprotected product: 14.3 g. Rf in To-EtOH (8:2) = 0.01 on $SiO_2$.

(c) Boc-Met-Ala-Ala-OMe: 15.8 g Boc-Met-$N_2H_3$, dissolved in 150 ml DMF, is activated at −20° C with 28.0 ml 4.2 N HCl in THF and 8.10 ml isoamyl nitrite. After 20 minutes activation at −15° C the solution is neutralized with 14.5 ml NEM, whereupon a solution of 14.3 g H-Ala-Ala-OMe.HCl (from (b)) in 75 ml DMF and 1 eq. NEM, is added. After the pH has been adjusted to 7.2 with NEM, the reaction mixture is kept at about 4° C for 48 hours. The NEM.HCl is then filtered off and the filtrate is evaporated to dryness. The residue is dissolved in 300 ml ethyl acetate and washed with water, 0.05N HCl, 5% $NaHCO_3$ and finally water again. After drying over $Na_2SO_4$, the filtrate is evaporated to dryness and the residue is crystallized from ethyl acetate:petroleum ether (1:1). Yield 16.2 g; melting point 128–129° C. Rf in To:EtOH (8:2) = 0.46 on $SiO_2$.

(d) Boc-Met-Ala-Ala-$N_2H_3$: 15.9 g Boc-Met-Ala-Ala-OMe from (c)) is dissolved in 160 ml methanol, and 16.0 ml hydrazine hydrate is added. After stirring for 3½ hours, 200 ml dry ether is added. After cooling to 0° C, the solid substance is filtered off. Yield 12.6 g; melting point 207–208° C. Rf in Am:iPro:Wa (10:4:5) = 0.41 on $SiO_2$.

The following peptides are prepared in a way corresponding to that indicated in 14:

15. Boc-Ala-Ala-Ala-$N_2H_3$; Rf in Am:iPro:Wa (10:4:5) = 0.44
16. Boc-Val-Ala-Ala-$N_2H_3$; Rf in Am:iPro:Wa (10:4:5) = 0.40
17. Boc-Met (→$O_2$)-Gly-Ala-$N_2H_3$; Rf in Am:i-Pro:Wa (10:4:5) = 0.37
18. Boc-Met-Glu(OtBu)-Ala-$N_2H_3$ (a) Z-Glu-OtBu-Ala-OMe: A solution of 3.37 g Z-Glu(OtBU)OH in 30 ml acetonitrile is added at 0° C to a suspension of 1.40 g H-Ala-OMe.HCl in 15 ml acetonitrile, after which 1 equivalent TAA followed by a solution of 2 g DCCI in 20 ml acetonitrile is added at −10° C. After stirring for 30 minutes at −10° C, the reaction mixture is subsequently stirred for a further 12 hours at room temperature. 30 ml water is then added, the DCHU formed is filtered off, and the filtrate is evaporated to dryness. The residue is dissolved in 100 ml ethyl acetate and subsequently washed with $H_2O$, 5% $NaHCO_3$ solution, 30% NaCl solution and water. After drying over $Na_2SO_4$, the filtrate is evaporated to dryness. Rf in Am:Py:Wa (5:3:2) = 0.89 on $SiO_2$.

(b) H-Glu(OtBu)-Ala-OMe.HCl: 2.53 g Z-Glu(OtBu)-Ala-OMe (from (a)) is dissolved in 30 ml methanol. After addition of 3.4 ml 2N HCl and 700 mg Pd/C, hydrogen is passed through the reaction mixture for 2½ (until evolution of $CO_2$ ceases). The catalyst is filtered off over Hyflo supplied by the Mansville Company, and the filtrate is evaporated to dryness. Yield: 1.95 g. Rf in Am:Py:Wa (5:3:2) = 0.71 on $SiO_2$.

(c) Boc-Met-Glu(OtBu)-Ala-OMe: this protected peptide is prepared in a way corresponding to that described in 14 (c). Yield 90%; melting point 103°–106° C. Rf in Am:Py:Wa (5:3:2) = 0.95 on $SiO_2$.

(d) Boc-Met-Glu(OtBu)-Ala-N₂H₃: Method corresponding to that of 14 (d). Yield 74.9%. Rf in Am:i-Pro:Wa (10:4:5) = 0.70 on SiO₂.

19. Boc-Met-Lys(Boc)-His-N₂H₃ (a) Z-Lys(Boc)-His-OMe: 22.8 g Z-Lys(Boc)-OH is dissolved in 200 ml DMF, after which 8.11 g HOBt is added. The mixture is cooled to −22° C, whereupon the following are added consecutively at −22° C: a solution of 14.52 g H-His-OMe.2HCl in 200 ml DMF, 2 eq. TAA and 12.36 g DCCI. After stirring for 20 minutes at −22° C, 2 hours at 0° C and 16 hours at room temperature, DCHU and TAA.HCl are filtered off and the filtrate is evaporated to dryness. The residue is dissolved in ethyl acetate and washed with water, NaHCO₃ solution (5%) and finally with water again. After drying over Na₂SO₄, the solution is evaporated to small bulk. Ether is added and the substance crystallizes out. Yield 19.2 g; melting point 138°–140° C. Rf in To:EtOH (8:2) = 0.35 on SiO₂.

(b) H-Lys(Boc)-His-OMe-HCl: 19 g Z-Lys(Boc)-His-OMe is dissolved in 210 ml DMF and 2 eq. HCl/DMF. After addition of Pd/C, hydrogen is passed in for 3 hours. The catalyst is filtered off and the filtrate is reduced to a volume of about 100 ml by evaporation. Rf in Am:Py:Wa (5:3:2) = 0.38 on SiO₂.

(c) Boc-Met-Lys(Boc)-His-OMe: the method is analogous to that of example 14 (c). Rf in Am:Py:Wa (5:3:2) = 0.24 on SiO₂.

(d) Boc-Met-Lys(Boc)-His-N₂H₃: the method is analogous to that of example 14 (d). Rf in Am:iPro:Wa (100:40:50) = 0.42 on SiO₂.

The following compounds are further prepared in an analogous fashion:

20. Desamino-Met-Ala-Ala-N₂H₃; Rf in Am:iPro:Wa (10:4:5) = 0.34 on SiO₂.

21. Boc-Leu-Glu(OtBu)-His-N₂H₃; Rf in Am:i-Pro:Wa (10:4:5) = 0.31 on SiO₂

22. Boc-Met-Ser-His-N₂H₃; Rf in Am:iPro:Wa (10:4:5) = 0.28 on SiO₂.

23. Boc-Ala-Ala-N₂H₃; Rf in Am:iPro:Wa (10:4:5) = 0.47 on SiO₂.

B. Synthesis of H-Phe-D-Lys(Boc)-Phe-Gly-OH and analogues. 101. H-Phe-D-Lys(Boc)-Phe-Gly-OH (a) Z-Phe-D-Lys(Boc)-OMe: 29.9 g Z-Phe-OH and 14.8 g HOBt are dissolved in 200 ml DMF. After cooling to −22° C the following are added consecutively: (1) a solution of 32.6 g H-D-Lys(Boc)OMe.HCl in 210 ml DMF and 1 eq. TAA, and (2) a solution of 22.7 g DCCI in 100 ml DMF. The whole is subsequently stirred by suitable mechanical means for 15 minutes at −22° C, for 2 hours at 0° C and for about 16 hours at room temperature.

The mixture is cooled to −20° C, after which the DCHU formed is filtered off and the filtrate is evaporated to dryness. The residue is dissolved in ethyl acetate and washed with water, a 5% solution of citric acid, 5% NaHCO₃ solution and again water, after which the solution is evaporated to dryness. The residue is crystallized from di-isopropyl ether/ether (1:5). Yield: 51.6 g; melting point 122/123° C. Rf in To:EtOH (8:2) = 0.60 on SiO₂.

(b) Z-Phe-D-Lys(Boc)-OH: 13.7 g Z-Phe-D-Lys(Boc)-OMe from (a) is dissolved in 180 ml dioxan/H₂O (9:1). After the addition of 15 ml 2N NaOH, the reaction mixture is stirred for 2 hours at room temperature and the pH is then adjusted to 7 with 1N HCl. The reaction mixture is subsequently reduced in volume to about 50 ml (dioxan-free) by evaporation, and 250 ml ethyl acetate is added. The mixture is washed with water and dried over Na₂SO₄. The Na₂SO₄ is filtered off and the filtrate is evaporated to dryness, after which the residue is crystallized from ether/petroleum ether (1:2). Yield: 11.3 g; melting point 72°/75° C. Rf in To:EtOH (8:2) = 0.12 on SiO₂; Rf in Am:Py:Wa (5:3:2) = 0.69 on SiO₂.

(c) Boc-Phe-Gly-OBzl: 1 eq. NEM is added to a solution of 12.6 g H-Gly-OBzl.HCl in 100 ml DMF, followed by a solution of 25.5 g Boc-Phe-ONP in 100 ml DMF. After stirring overnight at room temperature the reaction mixture is evaporated to dryness. The residue is dissolved in 300 ml ethyl acetate/water (5:1) and the resultant solution is washed with water.

After drying over Na₂SO₄, the volume of the filtrate is reduced to about 100 ml by evaporation; 50 ml petroleum ether and 250 ml dry ether are subsequently added. Yield 16.7 g; melting point 126°–127° C. Rf in To:EtOH (8:2) = 0.56 on SiO₂.

(d) H-Phe-Gly-OBzl.HCl: 8.25 g Boc-Phe-Gly-OBzl is dissolved in 120 ml methylene chloride and HCl-gas is passed in with stirring and cooling (ice/water) for 1 hour.

The introduction of HCl is stopped after 1 hour and the reaction mixture is evaporated to dryness. Yield 6.98 g of a foam-like product. Rf in To:EtOH (8:2) = 0.33 on SiO₂.

(e) Z-Phe-D-Lys(Boc)-Phe-Gly-OBzl: The method is analogous to the method described in (a). Reagents needed: 9.25 g Z-Phe-D-Lys(Boc)-OH (from (b)), 2.92 g HOBt, 6.98 g H-Phe-Gly-OBzl.HCl and 4.12 g DCCI. Crystallization from: ethyl acetate/petroleum ether. Yield: 12.0 g; melting point 157°–159° C.

(f) H-Phe-D-Lys(Boc)-Phe-Gly-OH: 4.11 g Z-Phe-D-Lys(Boc)-Phe-Gly-OBzl is dissolved in 75 ml DMF. After addition of Pd/C, hydrogen is passed into the mixture for 3 hours. The catalyst is filtered off over hyflo/asbestos and the filtrate is evaporated to dryness. Yield: 2.9 g. Rf in Bu:Py:Ac:Wa (4:0.75:0.25:1) = 0.46 on SiO₂.

The following peptides were prepared under conditions and in a manner identical to that given in the preceding example 101:

102. H-Trp-D-Lys(Boc)-Phe-Gly-OH; Rf in Bu:Py:Ac:Wa (4:0.75:0.25:1) = 0.52 on SiO₂

103. H-Leu-D-Lys(Boc)-Phe-Gly-OH; Rf in Bu:Py:Ac:Wa (4:0.75:0.25:1) = 0.40 on SiO₂

104. H-Val-D-Lys(Boc)-Phe-Gly-OH; Rf in Bu:Py:Ac:Wa (4:0.75:0.25:1) = 0.42 on SiO₂

105. H-Ala-D-Lys(Boc)-Phe-Gly-OH; Rf in Bu;-Py:Ac:Wa (4:0.75:0.25:1) = 0.37 on SiO₂

106. H-Tyr-D-Lys(Boc)-Phe-Gly-OH; Rf in Bu:Py:Ac:Wa (4:0.75:0.25:1) = 0.48 on SiO₂

C. Synthesis of H-Lys(Boc)-Pro-Val-Gly-Lys(Boc)-Lys(Boc)-OH and analogues.

201. H-Lys(Boc)-Pro-Val-Gly-Lys(Boc)-Lys(Boc)-OMe (11-16 ACTH); C.A. 72, 13055 (1970);

202. H-Lys(Boc)-Pro-Val-Gly-Lys(Boc)-Lys(Boc)-NH₂ (11-16 ACTH-amide); C.A. 72, 13055 (1970);

203. H-Lys(Boc)-Pro-Val-Gly-Lys(Boc)-Lys(Boc)-Arg-Arg-Pro-NH₂ (11-19 ACTH-amide); C.A. 63, 16405a (1965);

204. H-Lys(Boc)-Pro-Val-Gly-Lys(Boc)-Lys(Boc)-Arg-Arg-Pro-Val-Lys(Boc)-Val-Tyr-Pro-OtBu: Helv. 44, 1136 (1961);

205. H-D-Lys(Boc)-Pro-Val-Gly-Lys(Boc)-Lys(Boc)-NH₂; (a) H-Pro-Val-Gly-Lys(Boc)-Lys(Boc)-

NH$_2$: 8.61 g Z-Pro-Val-Gly-Lys(Boc)-Lys(Boc)-NH$_2$ is dissolved in 110 ml methanol. After addition of Pd/C, hydrogen is passed into the mixture for 3 hours. The catalyst is filtered off over hyflo and the filtrate is evaporated to dryness. Yield: 7.27 g. Rf in Am:Py:Wa (5:3:2) = 0.36 on SiO$_2$.

(b) Z-D-Lys(Boc)-Pro-Val-Gly-Lys(Boc)-Lys(Boc)-NH$_2$: 4.18 g Z-D-Lys(Boc)-OH and 1.62 g HOBt are dissolved in 30 ml DMF.

After cooling this solution to −22° C, solution of 7.26 g H-Pro-Val-Gly-Lys(Boc)-Lys(Boc)-OMe (from (a) in 30 ml DMF is added, followed by 2.47 g DCCI. After stirring for 15 minutes at −22° C, 2 hours at 0° C and 16 hours at room temperature, the DCHU formed is filtered off and the filtrate is evaporated to dryness.

The residue is dissolved in ethyl acetate and washed consecutively with citric acid solution, a solution of NaHCO$_3$ (5%) and a solution of NaCl (30%), after which it is dried over Na$_2$SO$_4$. The solution is evaporated to dryness and the residue is crystallized from ethyl acetate. Yield: 9.1 g; melting point 114°–119° C. Rf in To:EtOH (8:2) = 0.20 on SiO$_2$.

(c) H-D-Lys(Boc)-Pro-Val-Gly-Lys(Boc)-Lys(Boc)-NH$_2$: 3.68 g of the protected peptide obtained in (b) is dissolved in 50 ml methanol.

After the addition of Pd/C, hydrogen is passed in for 4 hours. The catalyst is then filtered off over Hyflo and the filtrate is evaporated to dryness. Yield: 3.2 g; Rf in Bu:Ac:Wa (10:1:3) = 0.56 on SiO$_2$.

Dissolving this product in a methanolic solution of HCl gives the corresponding peptide HCl salt.

206. H-Lys(Boc)-Pro-Val-Gly-Lys(Boc)-Lys(Boc)-OH Obtained by alcaline hydrolysis of the corresponding methyl ester, described in 201.

D. The synthesis of peptides obtained by coupling peptides noted under (A.) with peptides noted under (B.) by means of the azide method.

301. Boc-Met-Ala-Ala-Ala-D-Lys(Boc)-Phe-Gly-OH (14 and 105) 1.62 g Boc-Met-Ala-Ala-N$_2$H$_3$ is dissolved in 20 ml DMF. After cooling the solution to −20° C, 1,68 ml 4.74N HCl/THF is added, followed by 0.60 ml isoamylnitrite. After stirring for 20 minutes at −15° C, 0.6 ml NEM, a solution of 2.3 g H-Ala-D-Lys(Boc)-Phe-Gly-OH in 20 ml DMF and 1.68 ml 4.74N HCl/THF are added. The pH of the reaction mixture is adjusted to 7.2 with NEM, after which it is kept at about 4° C for 2 days. The NEM.HCl is then filtered off, and the filtrate evaporated to dryness. The residue is dissolved in 125 ml sec.butanol/CHCl$_3$ (2:3) and 25 ml H$_2$O, after which it is washed consecutively with water, 5% citric acid solution and again with water. After drying over Na$_2$SO$_4$, the filtrate is evaporated to dryness. The residue is dissolved in 40 ml methanol, to which 160 ml water is then added, after which the solid substance is filtered off and dried. Yield: 2.6 g; Rf in Bu:Py:Ac:Wa (4:0.75:0.25:1) = 0.62 on SiO$_2$; Melting point 202°–203° C with decomposition.

The following peptides are prepared under the same conditions as 301:

302. Boc-Met-Ala-Ala-Phe-D-Lys(Boc)-Phe-Gly-OH (14 and 101) Rf in Bu:Py:Ac:Wa (4:0.75:0.25:1) = 0.63 on SiO$_2$; melting point 215°–216° C (decomposition).

303. Boc-Ala-Ala-Ala-Phe-D-Lys(Boc)-Phe-Gly-OH (15 and 101) Rf = 0.59

304. Boc-Val-Ala-Ala-Phe-D-Lys(Boc)-Phe-Gly-OH (16 and 101); Rf = 0.61

305. Boc-Met(→ O$_2$)-Gly-Ala-Phe-D-Lys(Boc)-Phe-Gly-OH (17 and 101); Rf = 0.49

306. Boc-Met-Glu(OtBu)-Ala-Phe-D-Lys(Boc)-Phe-Gly-OH (18 and 101); Rf = 0.64

307. Desamino-Met-Ala-Ala-Phe-D-Lys(Boc)-Phe-Gly-OH (20 and 101); Rf = 0.67

308. Boc-Ala-Ala-Phe-D-Lys(Boc)-Phe-Gly-OH (23 and 101); Rf = 0.50

309. Boc-Ala-Phe-D-Lys(Boc)-Phe-Gly-OH; Rf = 0.51

310. Boc-Met-Glu(OtBu)-Ala-Ala-D-Lys(Boc)-Phe-Gly-OH (18 and 105); Rf = 0.64

311. Boc-Met(→ O$_2$)-Glu(OtBu)-His-Phe-D-Lys(Boc)-Phe-Gly-OH (2 and 101) 2.98 g Boc-Met(→ O$_2$)-Glu(OtBu)-His-N$_2$H$_3$ (4.82 mmol) is dissolved in 20 ml DMF and the solution is cooled to 0° C, after which 2.65 ml 5.46N HCl/THF is added to the cooled solution. The reaction mixture is then stirred for a while, after which it is further cooled to −20° C and 0.66 ml isoamyl nitrite is added. The mixture is stirred for 20 minutes at about −15° C, after which the same process is followed as described in 301.

The following peptides are prepared in a way corresponding to that described in 311:

312. Boc-Met-Glu(OtBu)-His-Phe-D-Lys(Boc)-Phe-Gly-OH (1 and 101); Rf = 0.69

313. Boc-Met-Glu(OtBu)-D-His-Phe-D-Lys(Boc)-Phe-Gly-OH (9 and 101); Rf = 0.71

314. Boc-Val-D-Glu(OtBu)-His-Phe-D-Lys(Boc)-Phe-Gly-OH (3 and 101); Rf = 0.65

315. Boc-Gly-Glu(OtBu)-His-Phe-D-Lys(Boc)-Phe-Gly-OH (4 and 101); Rf = 0.60

316. Boc-D-Met-Glu(OtBu)-His-Phe-D-Lys(Boc)-Phe-Gly-OH (5 and 101); Rf = 0.68

317. Boc-β-Ala-Glu(OtBu)-His-Phe-D-Lys(Boc)-Phe-Gly-OH (6 and 101); Rf = 0.62.

318. Boc-(α-Met)Ala-Glu(OtBu)-His-Phe-D-Lys(Boc)-Phe-Gly-OH (7 and 101); Rf = 0.60

319. Boc-Val-Glu(OtBu)-D-His-Phe-D-Lys(Boc)-Phe-Gly-OH (10 and 101); Rf = 0.64

320. Boc-Met-Gln-His-Phe-D-Lys(Boc)-Phe-Gly-OH (11 and 101); Rf = 0.75

321. Desamino-Met-Glu(OtBu)-His-Phe-D-Lys(Boc)-Phe-Gly-OH (12 and 101); Rf = 0.58

322. Boc-Met-Glu(OtBu)-His-Trp-D-Lys(Boc)-Phe-Gly-OH (1 and 102); Rf = 0.70

323. Boc-Met-Glu(OtBu)-His-Leu-D-Lys(Boc)-Phe-Gly-OH (1 and 103); Rf = 0.65

324. Boc-Met-Glu(OtBu)-His-Val-D-Lys(Boc)-Phe-Gly-OH (1 and 104); Rf = 0.70

325. Boc-Leu-Glu(OtBu)-His-Leu-D-Lys(Boc)-Phe-Gly-OH (21 and 103); Rf = 0.66

326. Boc-Met-Ser-His-Phe-D-Lys(Boc)-Phe-Gly-OH (22 and 101); Rf = 0.76

327. Boc-Met-Lys(Boc)-His-Phe-D-Lys(Boc)-Phe-Gly-OH (19 and 101); Rf = 0.69

328. N-acetyl-Met-Ala-Ala-Phe-D-Lys(Boc)-Phe-Gly-OH (N-acetyl-Met-Ala-Ala-N$_2$H$_3$ is prepared under the same conditions and in the way described in 14, with the proviso that in this case N-acetyl-Met-N$_2$H$_3$ is used instead of Boc-Met-N$_2$H$_3$). Rf = 0.55

329. Boc-Met-Glu(OtBu)-His-Tyr-D-Lys(Boc)-Phe-Gly-OH (1 and 106); Rf = 0.75

The Rf values for the above-named peptides apply to SiO$_2$ with Bu:Py:Ac:Wa (4:0.75:0.25:1) as eluent.

Although the invention has been described with reference to specific embodiments above, numerous variations and modifications will become evident to those skilled in the art, without departing from the scope and spirit of the invention as described above, defined in the appended claims, and as shown in the following examples.

EXAMPLE I

Preparation of
H-Met-Ala-Ala-Phe-D-Lys-Phe-Gly-D-Lys-Pro-Val-Gly-Lys-Lys-NH$_2$ (a) Boc-Met-Ala-Ala-Phe-D-Lys(Boc)-Phe-Gly-D-Lys(Boc)-Pro-Val-Gly-Lys(Boc)-Lys(Boc)-NH$_2$ 2.53 g Boc-Met-Ala-Ala-Phe-D-Lys(Boc)-Phe-Gly-OH (2.6 mmol) (see 302 above) and 422 mg HOBt (1.2 eq.) are dissolved in 25 ml DMF. The solution is cooled to 0° C, after which a solution of 2.48 g H-D-Lys(Boc)-Pro-Val-Gly-Lys(Boc)-Lys(Boc)-NH$_2$.HCl (2.5 mmol) in 20 ml DMF (205) and 1.1 eq. TEA are added. The temperature of the reaction mixture is adjusted to about 35° C, after which 857 mg DCCI (1.6 eq.) is added at this temperature and the whole is stirred overnight. The mixture is subsequently cooled to −20° C, the DCHU formed is filtered off, and the filtrate is evaporated to dryness. The residue is dissolved in 200 ml sec. butanol/CHCl$_3$ (2:3) and 50 ml H$_2$O, after which the solution is washed with water, 5% NaHCO$_3$ solution, again water and finally dried over Na$_2$SO$_4$. The Na$_2$SO$_4$ is filtered off and the filtrate is evaporated to dryness. Yield: 4.2 g. Rf in Bu:Ac:Wa (10:1:3) = 0.75 on SiO$_2$.

(b) H-Met-Ala-Ala-Phe-D-Lys-Phe-Gly-D-Lys-Pro-Val-Gly-Lys-Lys-NH$_2$.acetate 3.97 g Of the 4.2 g yield above Boc-Met-Ala-Ala-Phe-D-Lys(Boc)-Phe-Gly-D-Lys(BOC)-Pro-Val-Gly-Lys(Boc)-Lys(Boc)-NH$_2$ is dissolved in 80 ml 90% TFA, and the solution is stirred under nitrogen and in the dark for 1½ hours at room temperature.

The reaction mixture is then added dropwise to 500 ml dry ether. The solid substance is filtered off, washed with ether and dried, after which the residue is dissolved in t.butanol/H$_2$O (1:1) and stirred with an ion exchange-resin in acetate form. After stirring for 1 hour, the ion exchange resin is filtered off and the filtrate is evaporated to dryness. The crude product is subjected to counter-current purification (system sec.-butanol/0.1% TFA). The collected fractions are evaporated to dryness and the residue is dissolved in t.butanol/H$_2$O (1:1) after which it is again treated with the ion exchange resin in acetate form and filtered. The filtrate is evaporated to dryness. Yield 2.27 g (65.8%); Rf in Bu:Py:Ac:Wa (38:24:8:30) = 0.40 on Woelm.

EXAMPLE II

Preparation of H-Met(→ O$_2$)-Ala-Ala-Phe-D-Lys-Phe-Gly-D-Lys-Pro-Val-Gly-Lys-Lys-NH$_2$.acetate 2.0 g H-Met-Ala-Ala-Phe-D-Lys-Phe-Gly-D-Lys-Pro-Val-Gly-Lys-Lys-NH$_2$.acetate (from example I) is dissolved in 10 ml H$_2$O, after which 0.25 ml 0.5M ammonium molybdate, 1.25 ml 4M HClO$_4$ and 0.75 ml 30% H$_2$O$_2$ are added. The whole is then stirred for 4 hours at room temperature, after which 50 ml tert.butanol/H$_2$O (1:1) and 1 g suitable ion exchange resin (Dowex 2 × 8) in acetate form are added to the reaction mixture. After stirring for 30 minutes the ion exchange resin is filtered off and the filtrate is evaporated to dryness. Yield: 1.9 g; Rf in Bu:Py:Ac:Wa (38:24:8:30) = 0.32 on Woelm

EXAMPLE III

Preparation of H-Met(→ O)-Ala-Ala-Phe-D-Lys-Phe-Gly-D-Lys-Pro-Val-Gly-Lys-Lys-NH$_2$.acetate 0.06 mol Of the peptide obtained in Example I is dissolved in 5 ml acetic acid, after which 15 μl 30% hydrogen peroxide is added. The solution is stirred for 1 hour at room temperature, after which a suspension of 20 mg platinum-black in 2.5 ml glacial acetic acid is added. The mixture is then stirred for 30 minutes, after which it is filtered. The filtrate is evaporated to dryness under vacuum and the residue is added to 10 ml tert.butanol/water. The mixture is then freeze-dried. Rf in Bu:Py:Ac:Wa (38:24:8:30) = 0.29 on Woelm.

EXAMPLE IV

Preparation of H-Met(→ O$_2$)-Glu-His-Phe-D-Lys-Phe-Gly-D-Lys-Pro-Val-Gly-Lys-Lys-NH$_2$.acetate 4.0 g Of the peptide prepared in 311 above is coupled to peptide 205 using the DCCI/HOBt method as described in Example I(a). The protected end product has an Rf in Bu:Ac:Wa (10:1:3) of 0.73 on SiO$_2$.

The deprotection and further working-up are performed in the way described in Example I(b). Yield: 1.55 g; Rf in Bu:Py:Ac:Wa (38:24:8:30) = 0.19 on Woelm.

EXAMPLE V

The acetates of the following peptides are obtained under the same conditions and in the way corresponding to that described in Example I:

1. H-Met-Ala-Ala-Ala-D-Lys-Phe-Gly-D-Lys-Pro-Val-Gly-Lys-Lys-NH$_2$ (301 and 205); Rf = 0.20
2. H-Ala-Ala-Ala-Phe-D-Lys-Phe-Gly-D-Lys-Pro-Val-Gly-Lys-Lys-NH$_2$ (from 303 and 205 above); Rf = 0.35
3. H-Val-Ala-Ala-Phe-D-Lys-Phe-Gly-D-Lys-Pro-Val-Gly-Lys-Lys-NH$_2$ (from 304 and 205 above); Rf = 0.42
4. H-Met(→ O$_2$)-Gly-Ala-Phe-D-Lys-Phe-Gly-D-Lys-Pro-Val-Gly-Lys-Lys-NH$_2$ (from 305 and 205 above); Rf = 0.19
5. H-Met-Glu-Ala-Phe-D-Lys-Phe-Gly-D-Lys-Pro-Val-Gly-Lys-Lys-NH$_2$ (from 306 and 205 above); Rf = 0.34
6. Desamino-Met-Ala-Ala-Phe-D-Lys-Phe-Gly-D-Lys-Pro-Val-Gly-Lys-Lys-NH$_2$ (from 307 and 205 above); Rf = 0.47
7. H-Ala-Ala-Phe-D-Lys-Phe-Gly-D-Lys-Pro-Val-Gly-Lys-Lys-NH$_2$ (from 308 and 205 above); Rf = 0.40
8. H-Ala-Phe-D-Lys-Phe-Gly-D-Lys-Pro-Val-Gly-Lys-Lys-NH$_2$ (from 309 and 205 above); Rf = 0.42
9. H-Met-Gly-Ala-Ala-D-Lys-Phe-Gly-D-Lys-Pro-Val-Gly-Lys-Lys-NH$_2$ (from 310 and 205 above); Rf = 0.18
10. H-Met-Glu-His-Phe-D-Lys-Phe-Gly-D-Lys-Pro-Val-Gly-Lys-Lys-NH$_2$ (from 312 and 205 above); Rf = 0.29
11. H-Met-Glu-His-Phe-D-Lys-Phe-Gly-Lys-Pro-Val-Gly-Lys-Lys-NH$_2$ (from 312 and 202 above); Rf = 0.36
12. H-Met-Glu-His-Phe-D-Lys-Phe-Gly-Lys-Pro-Val-Gly-Lys-Lys-OMe (from 312 and 201 above); Rf = 0.52

13. H-Met-Ala-Ala-Ala-D-Lys-Phe-Gly-Lys-Pro-Val-Lys-Lys-OMe (from 301 and 201 above); Rf = 0.30

14. H-Met-Glu-D-His-Phe-D-Lys-Phe-Gly-D-Lys-Pro-Val-Gly-Lys-Lys-NH₂ (from 313 and 205 above); Rf = 0.31

15. H-Val-D-Glu-His-Phe-D-Lys-Phe-Gly-D-Lys-Pro-Val-Gly-Lys-Lys-NH₂ (from 314 and 205 above); Rf = 0.25

16. H-Gly-Glu-His-Phe-D-Lys-Phe-Gly-D-Lys-Pro-Val-Gly-Lys-Lys-NH₂ (from 315 and 205 above); Rf = 0.20

17. H-D-Met-Glu-His-Phe-D-Lys-Phe-Gly-D-Lys-Pro-Val-Gly-Lys-Lys-NH₂ (from 316 and 205 above); Rf = 0.33

18. H-(α-Me)Ala-Glu-His-Phe-D-Lys-Phe-Gly-D-Lys-Pro-Val-Gly-Lys-Lys-NH₂ (from 318 and 205 above); Rf = 0.28

19. H-β-Ala-Glu-His-Phe-D-Lys-Phe-Gly-D-Lys-Pro-Val-Gly-Lys-Lys-NH₂ (from 317 and 205 above); Rf = 0.19

20. H-Met-Gln-His-Phe-D-Lys-Phe-Gly-D-Lys-Pro-Val-Gly-Lys-Lys-NH₂ (from 320 and 205 above); Rf = 0.32

21. Desamino-Met-Glu-His-Phe-D-Lys-Phe-Gly-D-Lys-Pro-Val-Gly-Lys-Lys-NH₂ (from 321 and 205 above); Rf = 0.37

22. H-Met-Glu-His-Trp-D-Lys-Phe-Gly-D-Lys-Pro-Val-Gly-Lys-Lys-NH₂ (from 322 and 205 above); Rf = 0.31

23. H-Met-Glu-His-Leu-D-Lys-Phe-Gly-D-Lys-Pro-Val-Gly-Lys-Lys-NH₂ (from 323 and 205 above); Rf = 0.27

24. H-Met-Glu-His-Val-D-Lys-Phe-Gly-D-Lys-Pro-Val-Gly-Lys-Lys-NH₂ (from 324 and 205 above); Rf = 0.28

25. H-Leu-Glu-His-Leu-D-Lys-Phe-Gly-D-Lys-Pro-Val-Gly-Lys-Lys-NH₂ (from 325 and 205 above); Rf = 0.25

26. H-Met-Ser-His-Phe-D-Lys-Phe-Gly-D-Lys-Pro-Val-Gly-Lys-Lys-NH₂ (from 326 and 205 above); Rf = 0.31

27. H-Met-Lys-His-Phe-D-Lys-Phe-Gly-D-Lys-Pro-Val-Gly-Lys-Lys-NH₂ (from 327 and 205 above); Rf = 0.15

28. N-acetyl-Met-Ala-Ala-Phe-D-Lys-Phe-Gly-D-Lys-Pro-Val-Gly-Lys-Lys-NH₂ (from 328 and 205 above); Rf = 0.50; and 29. H-Met-Glu-His-Tyr-D-Lys-Phe-Gly-D-Lys-Pro-Val-Gly-Lys-Lys-NH₂ (from 329 and 205 above); Rf = 0.26.

All Rf values in Bu:Py:Ac:Wa (38:24:8:30) on Woelm.

EXAMPLE VI

The acetates of the following peptides (in which no N-terminal chain prolongation has been applied) are prepared in the same manner and under the same conditions as that described in Example I:

H-Phe-D-Lys-Phe-Gly-Lys-Pro-Val-Gly-Lys-Lys-NH₂ (from 101 and 202 above); Rf = 0.11

H-Phe-D-Lys-Phe-Gly-D-Lys-Pro-Val-Gly-Lys-Lys-NH₂ (from 101 and 205 above); Rf = 0.13

H-Phe-D-Lys-Phe-Gly-Lys-Pro-Val-Gly-Lys-Lys-OMe (from 101 and 201 above); Rf = 0.25

H-Phe-D-Lys-Phe-Gly-Lys-Pro-Val-Gly-Lys-Lys-Arg-Arg-Pro-NH₂ (from 101 and 203 above); Rf = 0.01

H-Phe-D-Lys-Phe-Gly-Lys-Pro-Val-Gly-Lys-Lys-Arg-Arg-Pro-Val-Lys-Val-Tyr-Pro-OH (from 101 and 204 above); Rf = 0.05

H-Ala-D-Lys-Phe-Gly-D-Lys-Pro-Val-Gly-Lys-Lys-NH₂ (from 105 and 205 above); Rf = 0.12.

Rf values were measured on SiO₂ with Bu:Py:Ac:Wa (2:0.75:0.25:1) as eluent.

EXAMPLE VII

The following peptides, preparation of which is described in Example V, are oxidized to the corresponding sulphones under the same conditions and in the way described in Example II. These peptides are obtained as acetates.

H-Met(→ O₂)-Ala-Ala-Ala-D-Lys-Phe-Gly-D-Lys-Pro-Val-Gly-Lys-Lys-NH₂ Rf = 0.16

Desamino-Met(→ O₂)-Ala-Ala-Phe-D-Lys-Phe-Gly-D-Lys-Pro-Val-Gly-Lys-Lys-NH₂ Rf = 0.12

H-Met(→ O₂)-Glu-His-Phe-D-Lys-Phe-Gly-D-Lys-Pro-Val-Gly-Lys-Lys-NH₂ Rf = 0.14

H-Met(→ O₂)-Glu-His-Phe-D-Lys-Phe-Gly-Lys-Pro-Val-Gly-Lys-Lys-OMe Rf = 0.22

Desamino-Met(→ O₂)-Glu-His-Phe-D-Lys-Phe-Gly-D-Lys-Pro-Val-Gly-Lys-Lys-NH₂ Rf = 0.17.

Rf values were measured on Woelm with Bu:Py:Ac:Wa (38:24:8:30) as eluent.

EXAMPLE VIII

The following peptides, preparation of which is described in Example V, are oxidized to the corresponding sulphoxides under the same conditions and in the way described in Example III. The peptides are obtained as acetates:

H-Met(→ O)-Glu-His-Phe-D-Lys-Phe-Gly-Lys-Pro-Val-Gly-Lys-Lys-NH₂ Rf = 0.19

H-Met(→ O)-Glu-His-Phe-D-Lys-Phe-Gly-D-Lys-Pro-Val-Gly-Lys-Lys-NH₂ Rf = 0.21

Desamino-Met(→ O)-Ala-Ala-Phe-D-Lys-Phe-Gly-D-Lys-Pro-Val-Gly-Lys-Lys-NH₂ Rf = 0.10.

Rf values were measured on Woelm with Bu:Py:Ac:Wa (38:24:8:30) as eluent.

EXAMPLE IX

Preparation of
H-Met-Ala-Ala-Phe-D-Lys-Phe-Gly-Lys-Pro-Val-Gly-Lys-Lys-OH 3.3 g Boc-Met-Ala-Ala-Phe-D-Lys(Boc)-Phe-Gly-OH (302) and 571.0 mg HOOBt are dissolved in 20 ml DMF, after which the solution is cooled at 0° C.

DCCI (760 mg) is added to this solution. The mixture is stirred for 1 hour at 0° C and about 16 hours at room temperature. The precipitate (DCHU) is filtered off and the filtrate is evaporated. The residue obtained (3.8 g), being the corresponding benztriazine-ester of the above starting peptide, and 4.06 g of the peptide H-Lys(Boc)-Pro-Val-Gly-Lys(Boc)-Lys(Boc)-OH (206) are dissolved in 50 ml DMF. The mixture is stirred for about 16 hours and then evaporated to dryness. The residue is dissolved in 200 ml sec. butanol/chloroform (2:3) and washed with water, 0.01 HCl and again water. The solution is dried on Na₂SO₄ and then filtered and evaporated to dryness. Yield 6.7 g.

In the manner, described in Example Ib the peptide obtained is deprotected. Yield 4.0 g. Rf in Bu:Py:Ac:Wa (38:24:8:30) = 0.35 on Woelm.

EXAMPLE X

Zinccomplex

Of a solution of zinc chloride, containing 50 mg of zinc per ml, 1.5 ml are added to a solution of 31.5 mg of $Na_2HPO_4 \cdot 2H_2O$ in 30 ml of distilled water. The precipitate of zinc phosphate formed is dissolved again by adding 4N HCl. Then 175 mg of NaCl and 0.5 of benzyl alcohol are added to this mixture. Then 1.5 mg of the peptide H-Met-Ala-Ala-Phe-D-Lys-Phe-Gly-D-Lys-Pro-Val-Gly-Lys-Lys-$NH_2$ are dissolved in this mixture and then enough 1N sodium hydroxide to adjust the pH of the mixture to 8.5. After that the volume is completed to 50 ml with distilled water.

1 ml of the suspension contains:
30 μg of the peptide
1.5 mg of zinc
0.63 mg of $Na_2HPO_4 \cdot 2H_2O$
3.5 mg of NaCl
10 mg of benzylalcohol.

The 1 ml suspension is lyophilized and stored in an ampoule. By the addition of 1 ml sterilized water to the ampoule, the suspension is ready for injection purposes.

EXAMPLE XI

Tablet

A granulate is prepared consisting of 2.5 mg carboxymethylcellulose, 20.0 mg starch and 68.5 mg lactose. This granulate is carefully mixed with a mixture consisting of 7.5 mg of the peptide of Example I, 1 mg of talcum and 0.5 mg of magnesium stearate, after which the mixture is compressed to a tablet of 100 mg.

EXAMPLE XII

Injection preparation peptide of Example I; 5.0 μg
NaCl; 9.0 mg
methyloxybenzoate; 1.2 mg
distilled, pyrogen-free water; 1.0 ml

EXAMPLE XIII

Capsule

Hard shell gelatin capsule containing
peptide of Example I; 0.5 mg
magnesium stearate; 1.45 mg
povidone; 5.5 mg
mannitol; 137.0 mg

We claim as our invention:

1. Compounds of the formula: A-L-B-D-Lys-L-Phe-Gly-(L or D)Lys-L-Pro-L-Val-Gly-L-Lys-L-Lys-X and their functional derivatives, wherein:

A is an N-terminal chain prolongation selected from the group consisting of:
   (1) hydrogen, and
   (2) the N-acyl radicals derived from:
      (a) alkyl carboxylic acids having from one to about six carbon atoms,
      (b) aralkyl carboxylic acids having from seven to about ten carbon atoms,
      (c) amino acids selected from the group consisting of Met, Met(→ O), Met (→ $O_2$), Glu, Ser, His, Phe, Arg, Lys, Trp, Gly, Val, Leu, Ala, Ileu, β-Ala, (α-Me) Ala, Pro, Tyr, and Thr,
      (d) peptides comprising two or three α-amino acids,
      (e) the N-alkylcarbonyl or N-aralkylcarbonyl derivatives of said amino acids, and
      (f) the N-alkylcarbonyl or N-aralkylcarbonyl derivatives of said peptides,
   wherein the alkyl moiety in (e) and (f) has from one to about six carbon atoms, and wherein the aralkyl moiety in (e) and (f) has from seven to about ten carbon atoms;

B is an amino acid residue selected from the group consisting of Phe, Trp, Tyr and —NH—CH—$R_1$—CO—, wherein $R_1$ is hydrogen or alkyl from one to about six carbon atoms; and X is a member selected from the group consisting of hydroxy, esterified hydroxy radicals of from one to eighteen carbon atoms, unsubstituted amino radicals, and substituted amino radicals selected from the group consisting of mono-alkyl (one to six carbons) amino, dialkyl-(one to six carbons) amino radicals, and radicals derived from amino acids or peptides having the sequence 17, 17-18, 17-19, up to and including 17-24 of the ACTH molecule, or a C-terminal ester or amide thereof, with the proviso that Arg may be replaced by Lys.

2. Compounds as recited in claim 1, wherein X is an unsubstituted amino radical.

3. Compounds as recited in claim 1, wherein A is a peptide comprising two or three amino acids selected from the group consisting of Met, Met (→ O), Met (→ $O_2$), Glu, Ser, His, Phe, Arg, Lys, Trp, Gly, Val, Leu, Ala, Ile, β-Ala, Ala, Tyr, and Thr.

4. Compounds as recited in claim 1, wherein B represents the amino acid residue Phe or Ala.

5. Compounds as recited in claim 1, wherein A is a radical selected from the group consisting of U-$Q_1$, U-$Q_2$-$Q_1$, of U, $Q_3$-$Q_2$-$Q_1$, wherein:

U is selected from the group consisting of hydrogen, N-alkylcarbonyl of from one to about six carbons, and N-aralkylcarbonyl from seven to about ten carbon atoms;

$Q_1$ is selected from the group amino-acid residues consisting of L-His, D-His, or NH-Z-CO, wherein Z is an unsubstituted, monohydroxy-substituted, or mono-amino substituted alkylene or alkylidene moiety of from one to about six carbon atoms;

$Q_2$ is selected from the group of amino-acid residues consisting of L-Glu, D-Glu, L-Gln, D-Gln or -NH-Z-CO-; and $Q_3$ is selected from the group acid residues consisting of U-L-Met, U-L-Met(→ O), U-L-Met(→ $O_2$), U-D-Met, U-D-Met(→ O), U-D-Met(→ $O_2$), desamino-Met, desamino-Met(→ O), desamino-Met(→ $O_2$), and UNH-Z-CO-.

6. Compounds as recited in claim 5, wherein A represents the moiety $Q_3$-$Q_2$-$Q_1$, wherein $Q_1$, $Q_2$ and $Q_3$ have the meanings indicated in claim 5.

7. Compounds as recited in claim 1, wherein A is selected from the group consisting of H-Met-Glu-His, desamino-Met-Glu-His, H-Met-Ala-Ala and desamino-Met-Ala-Ala.

8. Compounds as recited in claim 1, wherein A is selected from the sulfoxides or sulfones of H-Met-Glu-His, desamino-Met-Glu-His, H-Met-Ala-Ala and desamino-Met-Ala-Ala.

9. Compounds as recited in claim 1, wherein the second lysine group is in its D-form.

10. The compound as recited in claim 9 wherein A is H-Met-Ala-Ala, B is Phe, and X is $NH_2$, or an acid addition salt thereof.

11. The compound as recited in claim 9 wherein A is H-Met(→ O$_2$)-Ala-Ala, B is Phe, and X is NH$_2$, or an acid addition salt thereof.

12. The compound as recited in claim 9 wherein A is H-Met(→ O)-Ala-Ala, B is Phe, and X is NH$_2$, or an acid addition salt thereof.

13. The compound as recited in claim 9 wherein A is H-Met(→ O$_2$)-Glu-His, B is Phe, and X is NH$_2$, or an acid addition salt thereof.

14. The compound as recited in claim 9 wherein A is H-Met(→ O$_2$)-Ala-Ala, B is Ala, and X is NH$_2$.

15. The compound as recited in claim 9 wherein A is desamino-Met(→ O$_2$)-Ala-Ala, B is Phe, and X is NH$_2$.

16. The compound as recited in claim 9 wherein A is desamino-Met(→ O)-Ala-Ala, B is Phe, and X is NH$_2$.

17. The compound as recited in claim 9 wherein A is H-Met(→ O)-Glu-His, B is Phe, and X is NH$_2$.

18. A pharmaceutical composition having conditioned flight inhibiting psychopharmacological properties comprising:
(A) a pharmaceutically effective amount of a compound of the formula: A-L-B-D-Lys-L-Phe-Gly-(L or D)Lys-L-Pro-L-Val-Gly-L-Lys-L-Lys-X and their functional derivatives, wherein:

A is an N-terminal chain prolongation selected from the group consisting of:
(1) hydrogen, and
(2) the N-acyl radicals derived from:
 (a) alkyl carboxylic acids having from seven to about six ten atoms,
 (b) aralkyl carboxylic acids having from one to about six carbon atoms,
 (c) amino acids selected from the group consisting of Met, Met (→ O), Met (→ O$_2$), Glu, Ser, His, Phe, Arg, Lys, Trp, Gly, Val, Leu, Ala, Ileu, β-Ala, (α-Me)Ala, Pro, Tyr, and Thr,
 (d) peptides comprising two or more α-amino acids,
 (e) the N-alkylcarbonyl or N-aralkylcarbonyl derivatives of said amino acids, and
 (f) the N-alkylcarbonyl or N-aralkylcarbonyl derivatives of said peptides,
wherein the alkyl moiety in (e) and (f) has from one to about six carbon atoms, and wherein the aralkyl moiety in (e) and (f) has from seven to about ten carbon atoms;

B is an amino acid residue selected from the group consisting of Phe, Trp, Tyr and —NH—CH-R$_1$—CO—, wherein R$_1$ is hydrogen or alkyl from one to about six carbon atoms; and X is a member selected from the group consisting of hydroxy, esterified hydroxy radicals of from one to eighteen carbon atoms, unsubstituted amino radicals, and substituted amino radicals selected from the group consisting of mono-alkyl (one to six carbon) amino, dialkyl-(one to six carbons) amino, and radicals, derived from amino acids or peptides having the sequence 17, 17-18, 17-19, up to and including 17-24 of the ACTH molecule, or a C-terminal ester or amide thereof, with the proviso that Arg may be replaced by Lys; or pharmaceutically acceptable and nontoxic functional derivative thereof; and (B) a pharmaceutically acceptable carrier therefor.

19. A composition of matter as recited in claim 18 wherein B represents the amino-acid residue Phe or Ala.

20. A composition of matter as recited in claim 18, wherein X is an unsubstituted amino radical.

21. A composition of matter as recited in claim 18, wherein A is a N-acyl radical selected from the group consisting of U-Q$_1$; U-Q$_2$, and Q$_3$-Q$_2$-Q$_1$, wherein:

U is selected from the group consisting of hydrogen, N-alkylcarbonyl of from one to about six carbons, and N-aralkylcarbonyl from seven to about ten carbon atoms;

Q$_1$ is selected from the group amino-acid residues consisting of L-His, D-His, or NH-Z-CO, wherein Z is an unsubstituted, monohydroxy substituted, or monoamino substituted alkylene or alkylidene moiety of from one to about six carbon atoms;

Q$_2$ is selected from the group of amino-acid residues consisting of L-Glu, D-Glu, L-Gln, D-Gln or -NH-Z-CO-; and Q$_3$ is selected from the group acid residues consisting of U-L-Met, U-L-Met(→ O), U-L-Met(→ O$_2$), U-D-Met, U-D-Met(→ O), U-D-Met(→ O$_2$), desamino-Met, desamino-Met(→ O), desamino-Met(→ O$_2$), and UNH-Z-CO-.

22. Compounds as recited in claim 21, wherein A is the moiety Q$_3$-Q$_2$-Q$_1$, wherein Q$_1$, Q$_2$ and Q$_3$ have the meanings indicated in claim 21.

23. Compounds as recited in claim 18, wherein A is selected from the group consisting of H-Met-Glu-His, desamino-Met-Glu-His, H-Met-Ala-Ala, and desamino-Met-Ala-Ala.

24. Compounds as recited in claim 18, wherein A is selected from the sulfoxides or sulfones of H-Met-Glu-His, desamino-Met-Glu-His, H-Met-Ala-Ala, and desamino-Met-Ala-Ala.

25. Compounds as recited in claim 18, wherein the second lysine group is in its D-form.

26. The compound as recited in claim 25, wherein A is H-Met-Ala-Ala, B is Phe, and X is NH$_2$.

27. The compound as recited in claim 25, wherein A is H-met(→ O$_2$)-Ala-Ala, B is Phe, and X is NH$_2$.

28. The compound as recited in claim 25, wherein A is H-Met(→ O)-Ala-Ala, B is Phe, and X is NH$_2$.

29. The compound as recited in claim 25, wherein A is H-Met(→ O$_2$)-Glu-His, B is Phe, and X is NH$_2$.

30. The compound as recited in claim 25, wherein A is H-Met(→ O$_2$)-Ala-Ala, B is Ala, and X is NH$_2$.

31. The compound as recited in claim 25, wherein A is desamino-Met(→ O$_2$)-Ala-Ala, B is Phe, and X is NH$_2$.

32. The compound as recited in claim 25, wherein A is desamino-Met(→ O)-Ala-Ala, B is Phe, and X is NH$_2$.

33. The compound as recited in claim 25, wherein A is H-Met(→ O$_2$)-Glu-His, B is Phe, and X is NH$_2$.

34. A composition of matter as recited in claim 18, wherein A is a peptide consisting of two or three amino acids selected from the group consisting of Met, Met (→ O), Met (→ O$_2$), Glu, Ser, His, Phe, Arg, Lys, Trp, Gly, Val, Leu, Ala, Ileu, β-Ala, (α-Me)Ala, Tyr and Thr.

* * * * *